United States Patent
Thibos et al.

(10) Patent No.: US 7,857,451 B2
(45) Date of Patent: Dec. 28, 2010

(54) SYSTEM AND METHOD FOR OPTIMIZING CLINICAL OPTIC PRESCRIPTIONS

(75) Inventors: Larry N. Thibos, Bloomington, IN (US); Arthur Bradley, Bloomington, IN (US); Raymond A. Applegate, Humble, TX (US)

(73) Assignees: Indiana University Research and Technology Corporation, Bloomington, IN (US); The University of Houston, Houston, TX (US)

(*) Notice: Subject to any disclaimer, the term of this patent is extended or adjusted under 35 U.S.C. 154(b) by 240 days.

(21) Appl. No.: 10/582,470

(22) PCT Filed: Dec. 13, 2004

(86) PCT No.: PCT/US2004/041694

§ 371 (c)(1),
(2), (4) Date: Jun. 12, 2006

(87) PCT Pub. No.: WO2005/058136

PCT Pub. Date: Jun. 30, 2005

(65) Prior Publication Data

US 2007/0115432 A1    May 24, 2007

(51) Int. Cl.
*A61B 3/00* (2006.01)

(52) U.S. Cl. .................................. 351/246; 351/221
(58) Field of Classification Search ................. 351/246, 351/212, 221
See application file for complete search history.

(56) References Cited

U.S. PATENT DOCUMENTS

| 5,777,719 | A * | 7/1998 | Williams et al. ............ 351/212 |
| 6,511,180 | B2 | 1/2003 | Guirao et al. |
| 2002/0186346 | A1 * | 12/2002 | Stantz et al. ................. 351/205 |
| 2003/0071967 | A1 | 4/2003 | Campin et al. |
| 2003/0133074 | A1 | 7/2003 | Pettit et al. |
| 2004/0054358 | A1 * | 3/2004 | Cox et al. ...................... 606/5 |

* cited by examiner

*Primary Examiner*—Joseph Martinez
*Assistant Examiner*—James R Greece
(74) *Attorney, Agent, or Firm*—Homer W. Faucett, III; Ice Miller LLP

(57) ABSTRACT

An method and system for determining the appropriate refractive prescription in a clinical optometry or opthalmology setting. Data in the form of aberrometric input, patient history and other information, and/or other environmental data is used to optimize a real-world prescription for an individual's optic needs through the use of a equivalent quadratic fitting calculation or a simulated through focus experiment.

24 Claims, 3 Drawing Sheets

SYSTEM AND METHOD FOR OPTIMIZING CLINICAL OPTIC PRESCRIPTIONS

STATEMENT REGARDING FEDERALLY SPONSORED RESEARCH AND DEVELOPMENT

Part of the work during the development of this invention was made with government support from the National Institutes of Health under grant numbers EY005109 and EY008520. The U.S. Government has certain rights in the invention.

BACKGROUND

The present invention relates to calculating the quality of vision and optical prescriptions for correcting optical imperfections in a patient's eyes.

Clinical optical prescriptions are calculated to determine the best combination of spherical and cylindrical lenses that optimize visual acuity for distant objects, thereby maximizing the quality of the retinal image. However, it has been found clinically that optimizing a prescription in the presence of high order aberrations as defined by many of the optic metrics used today does not always result in a prescription that causes the best focus as determined by a patient. Therefore, once an optic prescription for spherical and cylindrical correction is calculated, a clinician typically must use an iterative method for fine tuning that calculation in a trial and error fashion, as the patient compares the effect on vision while the clinician changes between slightly different corrective lenses. Since this method is time consuming, subjective, and requires clinical experience to practice accurately and efficiently, a method for objectively calculating an optimal clinical prescription without an iterative trial and error process is desired.

Further, in determining an optimal optical prescription, a clinician must also take into account the so-called refractionist's rule "maximum plus to best visual acuity." This requires a clinician to calculate a prescription wherein the spherical component of a myopic (nearsighted) eye is slightly undercorrected and a hyperopic (farsighted) eye is slightly overcorrected. Thus, currently, the calculation for the ideal optical focus is not necessarily the best clinical prescription, requiring a second calculation or iterative testing to determine the optimal optic prescription. Because iterative calculations or testing is time consuming, a method is needed for incorporating the "maximum plus to best visual acuity" rule into a method for optimizing clinical optic prescriptions.

Furthermore, many of today's eyecare clinics employ commercial aberrometers to measure the eye's higher order aberrations, and the lower-order, sphero-cylindrical aberrations are readily measured with an autorefractor. Modern clinical aberrometers (e.g., Shack-Hartmann wavefront-sensing technique or subjective ray-tracing technique) typically provide detailed maps of the eye's refracting properties across the entire pupil. Such aberration maps have the potential to accurately form the basis of wavefront-guided corrections of the eye (e.g., refractive surgery, IOLs, and contact lens design. However, detailed aberration maps contain a wealth of information that can overwhelm a clinician and impede interpretation. One way to reduce the complexity of an aberration map is to fit the map with a relatively small number of Zernike radial polynomials, simplifying the description. However, even a Zernike spectrum is complex, and its relationship to visual quality is complicated. Ultimately it is desired to reduce an aberration measurement to a single metric of quality of vision, allowing a clinician to objectively evaluate the current quality of vision and the potential for improvement. Such an objective definition of the visual quality of the eye in a single metric would allow the evaluation of various methods of treatment (e.g., spectacle, IOL, contact lens, refractive surgery, etc.), and would be greatly appreciated in the art.

One strategy to simplify an aberration measurement into a metric of image quality includes the use of the second order aberrations of astigmatism and defocus in an aberration map to prescribe a correcting lens that eliminates second-order aberrations. Unfortunately, several studies show that eliminating the second-order Zernike aberrations may not optimize either the subjective impression of best-focus or the objective measurement of visual performance. This phenomenon may be explained by the lack of a universally-accepted metric of image quality to establish an objective optimum-focus state for an aberrated eye. A useful metric of optical quality for the human eye is one that is highly correlated with visual performance, the subjective judgment of best focus, or other tasks that are optically limited. Traditional metrics such as Strehl ratio, root mean squared (RMS) wavefront error are widely used in ophthalmic optics, but they are not well-suited as a metric that is related to the subjective judgment of best focus for the eye. In fact, recent data suggests that calculations based on RMS error are poor predictors of visual acuity for aberrated retinal images. Therefore, a system for prescribing and evaluating clinical optic prescriptions should employ metrics that are good objective indicators of subjective visual acuity for aberrated retinal images.

One method for generating an optimized optic prescription is described in U.S. Pat. No. 6,511,180 to Guirao & Williams (the "Guirao Patent"). The Guirao Patent describes an iterative method for finding the optimum sphere, cylinder and axis parameters by simultaneously optimizing a metric of image quality. However, this method requires a great deal of computing power to perform, and may not optimize the visual quality, due to the metric employed. Further, this method does not incorporate the many clinical considerations into a method for determining an optic prescription that best suits a patient, and this patent is confined to the use of a small subset optical quality metrics to determine a refraction. Therefore, a method allowing multiple uses of multiple metrics of vision quality would be appreciated, greatly increasing the flexibility and utility of automated refraction and assessment of the visual consequences of different refractive treatments.

Further, an eye-care practitioner must take into consideration patient data, environmental data, and apply clinical judgment to adjust the optically optimized prescription. Failure to include these inputs can cause numerous unacceptable prescriptions. Each of these steps often requires subjective decisions based upon clinical experience, and must be made after or in addition to the calculations for optical optimizations based upon aberration measurements. Therefore, a method or system incorporating these clinical and patient considerations is desired. Further, an automated method or system to perform this task in a more accurate fashion utilizing less computing power is desired.

SUMMARY

The present invention relates to the quantification of visual quality, differential diagnosis of optical dysfunction, and the optimization of optical corrections to improve the quality of life of the individual patient. Specifically, a system and method of evaluating the optical quality and optical health of the eye, using this knowledge to provide an optical prescription is based on visual quality metrics combined with knowledge of the patient, optical needs, and the many clinical considerations that lead to improved quality of life derived from providing an customized optical correction.

According to one aspect of the present invention, a method for calculating an optimal refractive prescription comprises the steps of obtaining aberrometric data from a patient by way of an aberrometer, and thereafter using the aberrometric data to perform a equivalent quadratic fitting calculation to obtain an ideal optic prescription for the patient. Optionally, the method may comprise an additional step wherein the calculated ideal optic prescription is adjusted to maximize depth of focus for a particular use or distance. Finally, the method may be performed using a computer microprocessor.

According to another aspect of the present invention, a method for optimizing a refractive prescription comprises the steps of obtaining aberrometric data from a patient by way of an aberrometer, calculating the retinal image from the aberration data, and selecting and computing a metric of visual quality appropriate by simulating a through focus experiment appropriate for the visual task or tasks that wish to be optimized. Further, the method may include the step of selecting a prescription that maximizes a given quality of vision metric or multiple quality of vision metrics for specified distances. Optionally, the method may include the step of selecting a prescription that trades off maximal quality for increased depth of focus. Optionally, the method may comprise the additional step of adjusting the calculated optical prescription to maximize the utilization of the eye's depth of field. However, if the patient's vision is hyperopic, the method may comprise the additional step of adjusting the ideal optic prescription by increasing the positive prescription by less than about 0.5. Further the method may optionally comprise the step of including use of prescription information and other clinically relevant data that increases the quality of life of the patient by customizing the optical correction to best meet the patient visual needs.

DESCRIPTION OF THE INVENTION

Vision quality metrics have many uses in eye care. They are used to determine if a patient's vision is sub-normal, to discriminate between optical and neurological causes of reduced vision, to select appropriate methods of treatment, to monitor outcome of that treatment, and to optimize vision by additional follow-up treatments. When combined with additional information about previous health history, lifestyle, and vision needs, the ultimate aim is improved quality of life through improved optical quality of the patient's eyes.

Figure 1:
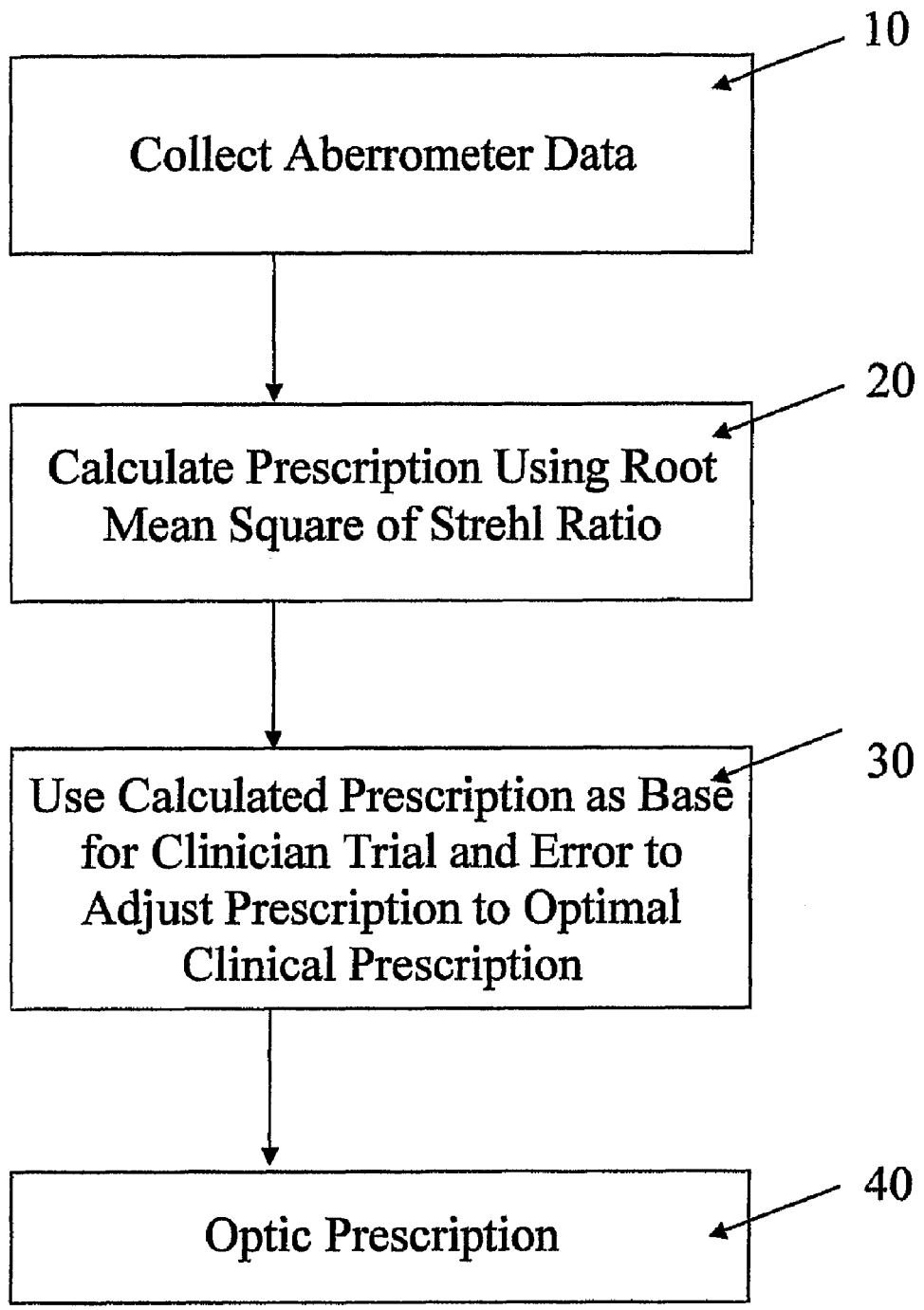
FIG. 1 is a flow chart illustrating prior art method steps for optimizing an optic prescription.
Figure 2:
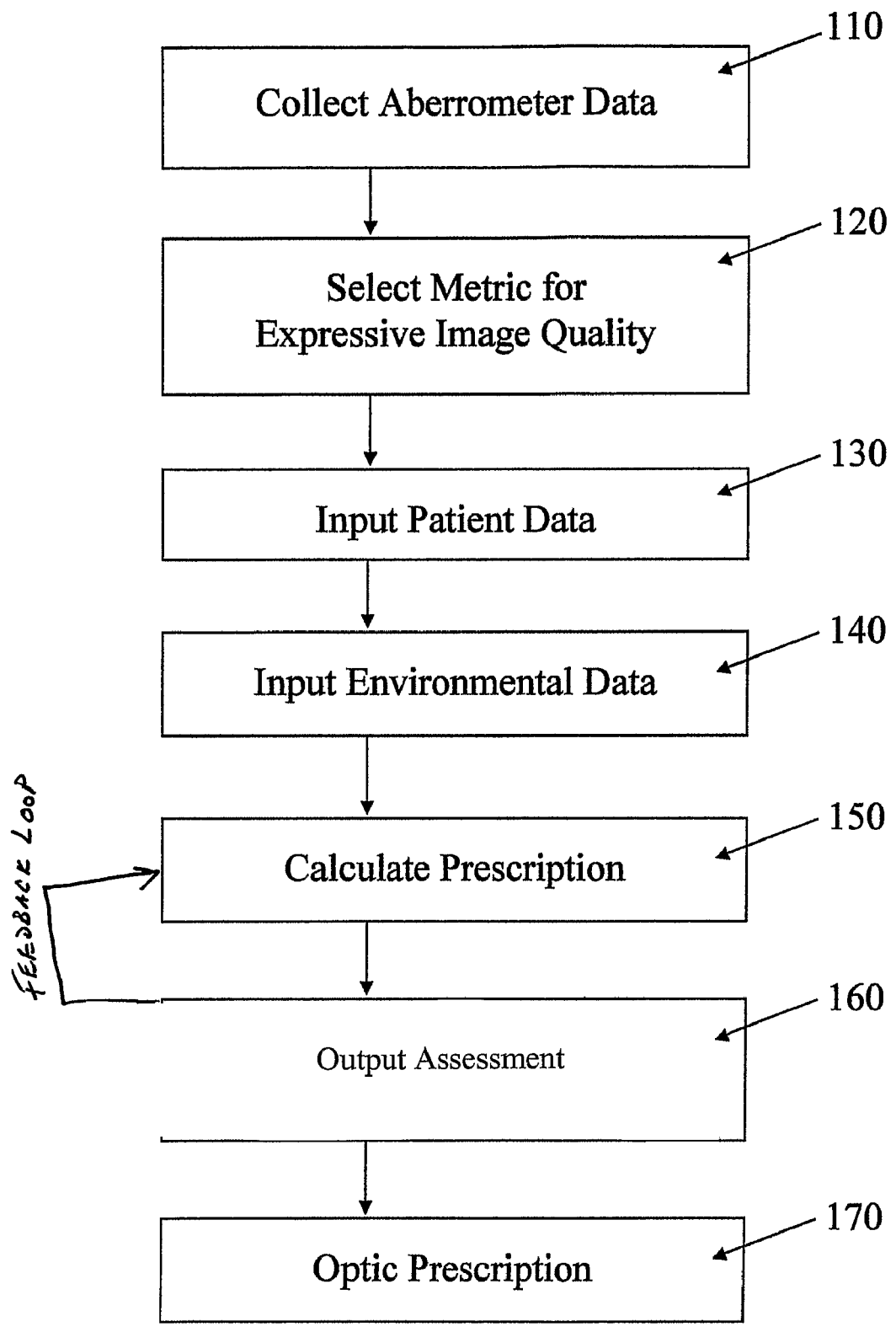
FIG. 2. is a flow chart illustrating exemplary method steps for optimizing an optic prescription according to one aspect of the present invention.

Referring to FIG. 2, a system and method for calculating a refractive prescription for an individual's needs, a flow chart for data input and integration for calculation is shown. As can be seen, the path to the final prescription represents one embodiment of the present invention. In comparison, FIG. 1 shows the prior art system of calculating an optically optimized refractive prescription from aberrometry data alone, optimized for a specified working distance. This prior art system is incomplete, as it requires additional clinical trial and error to obtain a clinically acceptable prescription, such as the classic eye care professional iteratively asking the patient to compare a first and second lens to optimize a refractive prescription for one particular mode of prescription (e.g. contact lenses, multifocal lenses, IOL's, glasses, etc.).

Instead, as shown in the method described in FIG. 2, clinical considerations and optometric and ophthalmic practice indicate that, in addition to the aberrometric data 110, metric selection 120, patient data 130, environmental data 140, and clinical considerations 160 result is a more complete system that makes more accurate judgments. These judgments are more complete, as they rely upon on multiple inputs and a feedback loop as illustrated in FIG. 2, as opposed to simply using aberrometric optimizations and then relying upon iterative trial and error used in the prior art systems as shown in FIG. 1. Furthermore, the present invention optimizes the metrics through the use of a feedback loop wherein the patient is allowed to participate in assessing the relative merits of each of the modes of refractive correction. For example, the present invention calculates an optimized refractive prescription for multiple modes of correction (each of which mode of prescription is automatically optimized without the use of iterative subjective input), a patient may be allowed to assess the relative merits of each of the modes of prescription of the refractive correction (e.g. whether the patient would prefer multifocal lenses, contact lenses, IOL's, etc.) through computer modeling.

Therefore, referring to FIG. 2, an embodiment of a method to optimize optic prescriptions may take the form of multiple steps. In particular, the steps would include obtaining aberrometry data 110 such as the vector of Zernike coefficients (or any other representation) defining an aberration map, pupil radius, wavelength of light employed in the aberrometer, and other appropriate data typically collected by an aberrometer. Further, the method suggests selecting a metric for expressing visual quality 120, which can take the form of several metrics employed in the art today, including those detailed below. Further, according to this method, patient data is obtained 130, such as the age of the patient, the patient's habitual prescription, and the type of correction contemplated (glasses, contact lenses, refractive surgery, inlays, etc.). Additional environmental data may be obtained 140, such as the manner in which the patient typically uses her eyes, the type of working environment the patient typically finds herself in, and the current temperature and humidity under which the aberrometry data is taken and the correction applied. Additionally, clinical considerations and nomograms may be entered for consideration, such as how quickly the clinician wishes to adjust the current prescription, and whether the clinician wishes to adjust the prescription to implement the refractionist's rule of maximum plus to best visual acuity. Finally, a calculation of an ideal prescription is made 150, using the selected metric/s to determine an objective best focus suitable for the visual task of interest, and that prescription is adjusted 160 to take into account the clinical considerations for optimizing subjective best focus, thereby leading to optic prescription 170. Each of these steps is addressed below.

A. Collecting Aberrometric Data

Referring to the first step illustrated in FIG. 1, aberrometric data is typically collected through a commercial aberrometer. The data collected by an aberrometer typically measures wavefront slope at multiple locations within the pupil for specific wavelength. These slopes can be used to reconstruct a monochromatic wavefront error map or using models of chromatic aberration to estimate the polychromatic wavefront errors of the eye. These error maps can be represented by a spectra of Zernike or Fourier coefficients. This data is typically collected from an aberrometer that employs a Shack-Hartmann wavefront-sensing technique or an objective or subjective ray tracing technique that provides detailed maps of the eye's refracting properties across the entire pupil. From this data, an aberration map can be formed by methods well known in the art, and the data can be stored on a connected computer to be used for calculating an ideal optic prescription according to calculations or software programs described in further detail below.

B. Calculating an Ideal Optic Prescription

As described herein, methods for determining an ideal optic refractive prescription for an eye are based upon optimizing visual quality by one of the two following methods: (1) a curve fitting method designed to find the nearest spherocylindrical approximation to the actual wavefront aberration map, and (2) a metric optimization through virtual through focus in which various amounts of spherical or cylindrical wavefront is added to or subtracted from an aberration map until the optical quality of the eye is maximized. One of ordinary skill in the art will appreciate that other methods such as least squares fitting may be used for calculating an ideal optic prescription instead of the three methods disclosed here. However, curve fitting, and metric optimization through virtual through focus are described in detail below.

1. Equivalent Quadratic Fitting

A first method for calculating an ideal optic prescription is equivalent quadratic fitting. Curvature is the property of wavefronts that determines focus. The sphero-cylindrical equivalent of an aberration map is that quadratic (i.e. a sphero-cylindrical) surface which best represents the map. This idea of representing an aberrated map with a quadratic surface is an extension of the ophthalmic technique of representing a quadratic surface with an "equivalent sphere." Thus, a reasonable way to fit an arbitrary wavefront with a quadratic surface is to match the curvature of the two surfaces at some reference point.

A variety of reference points can be selected, but a natural choice is the pupil center. Two surfaces that are tangent at a point and have exactly the same curvature in every meridian are said to "osculate". Thus, the surface sought in one aspect of this invention is the osculating quadric. A closed-form solution exists for the problem of deriving the power vector coordinates of the correcting lens from the Zernike coefficients of the wavefront by computing the Zernike expansion of the Seidel formulae for defocus and astigmatism. The results given in equation:

$$M = \frac{-c_2^0 4\sqrt{3} + c_4^0 12\sqrt{5} - c_6^0 24\sqrt{7} + \cdots}{r^2}$$

$$J_0 = \frac{-c_2^2 2\sqrt{6} + c_4^2 6\sqrt{10} - c_6^2 12\sqrt{14} + \cdots}{r^2}$$

$$J_{45} = \frac{-c_2^{-2} 2\sqrt{6} + c_4^{-2} 6\sqrt{10} - c_6^{-2} 12\sqrt{14} + \cdots}{r^2}$$

are truncated at the sixth Zernike order but could be extended to higher orders if warranted. However, testing has shown optimization through equivalent quadratic fitting to be an accurate predictor of a subjective best focus, unlike many other objective methods. Therefore, use of this equivalent quadratic fitting calculation has been shown to yield excellent clinical results. Further, alternative strategies can be centered on the pupil region of best optical quality or maximal photon efficiency.

2. Metric Optimization by Computer Simulation of Through Focus and Through-Astigmatism Another way to determine the focus error of an eye, and thereby calculate an ideal prescription, is to move an object axially along the line-of-sight until the retinal image of that object appears subjectively to be well focused. This procedure can be simulated mathematically by adding a spherical wavefront to the eye's aberration map and then computing the retinal image using methods of Fourier optics as further described by Thibos, Applegate, and Bradley in "Accuracy and Precision of Objective Refraction from Wavefront Aberrations," *Journal of Vision* (2003) (herein incorporated by reference).

The curvature of the added wavefront can be systematically varied to simulate a through-focus experiment that varies the optical quality of the eye and lens system over a range from good to bad. Given a suitable metric of optical quality, this computational procedure yields the optimum power M of the spherical correcting lens needed to maximize optical quality of the corrected eye. With this virtual spherical lens in place, the process can be repeated for "through-astigmatism" calculations to determine the optimum values of J0 and J45 needed to maximize image quality. With these virtual astigmatic lenses in place, the last step would be to fine-tune the determination of M by repeating the through-focus calculations. Optionally, a computer simulation of the Jackson Cross-cylinder test for axis and power of astigmatism could also be performed. Furthermore, one of ordinary skill in the art will appreciate that this method is not limited to optimize only spherical and astigmatic aberrations, but may be used to optimize a myriad of other refractive aberrations. Regardless of the aberration optimized through this method, the method shall be described as a "through focus" experiment herein.

This computational method captures the essence of refraction by successive elimination and refinement used clinically by mathematically simulating the effect of sphero-cylindrical lenses of various powers. That quadratic wavefront which maximizes the eye's optical quality when added to the eye's aberration map defines the ideal correcting lens, eliminating or reducing the need for clinical trial and error.

Figure 3A:
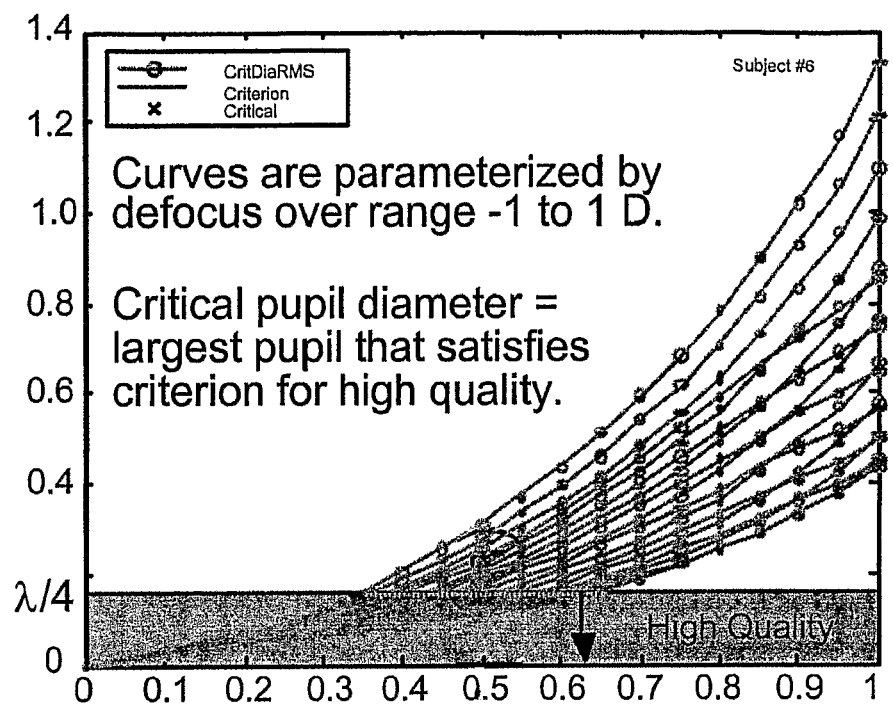
FIG. 3A is a graphical depiction of RMS wavefront error to pupil radius.
Figure 3B:
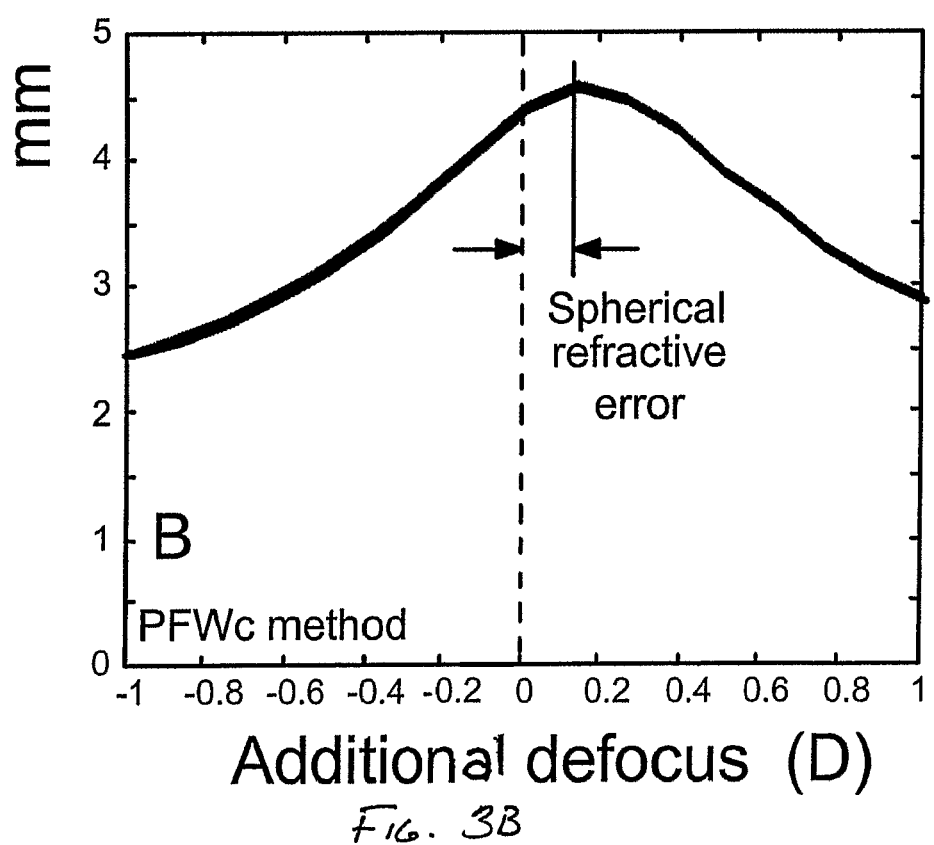
FIG. 3B is a set of critical radius values from the RMS wavefront error to pupil radius plotted as a function of defocus.

For example, FIGS. 3A and 3B display intermediate results for optimizing the pupil fraction metric PFWc (the metric described in further detail below). As shown in FIG. 3A, for each lens power over the range −1 to +1 Diopter ("D") (in 0.125 D steps) a curve is generated relating RMS wavefront error to pupil radius. Each of these curves crosses the criterion level ($\lambda/4$ in these calculations) at some radius value. That radius is interpreted as the critical radius since it is the largest radius for which the eye's optical quality is reasonably good. The set of critical radius values can then be plotted as a function of defocus, as shown in FIG. 3B. This through-focus function peaks at some value of defocus, which is taken as the optimum lens for this eye using this metric. Thus the full dataset of FIGS. 3A and 3B is reduced to a single number. Therefore, once a metric of optical quality is selected for optimization, this through focus method allows for computation of an ideal prescription.

C. Selecting a Metric for Optimization

As discussed above, calculating an ideal optic prescription in many cases first involves the selection of a metric that expresses overall image quality so that computation and interpretation can be more readily managed. In selecting a metric of optical quality for the human eye, a clinician typically wants to select a metric that is highly correlated with visual performance. However, a vast number of metrics are currently used in the optic and optometric arts, and the best metric for use in optimizing a patients optic prescription has not yet been proven or established in the fields of optometry and opthalmology. Therefore, one embodiment of the present invention anticipates the flexibility of utilizing any selected metric for expressing overall image quality. Those metrics that one may select to use may include those discussed by Thibos, Applegate, Hong, and Bradley in "Metrics of Optical Quality of the Eye," Journal of Vision, 2003 (herein incorporated by reference) and, but one of ordinary skill in the art will appreciate that any metric may be optimized using the methods described herein. Further, the following metrics are described in greater detail.

A perfect optical system has a flat wavefront aberration map and therefore metrics of wavefront quality are designed to capture the idea of flatness. Since a wavefront, its slope, and its curvature each admits to a different optical interpretation, meaningful scalar metrics based on all three are herein provided: the wavefront aberration map, the slope map, and the curvature map.

Flatness Metrics

Wavefront error describes optical path differences across the pupil that give rise to phase errors for light entering the eye through different parts of the pupil. Two common metrics of wavefront flatness follow.

$RMS_w$=Root-Mean-Squared Wavefront Error Computed Over the Whole Pupil (Microns)

$$RMS_w = \left[\frac{1}{A}\int_{pupil}(w(x,y) - \overline{w})^2 dxdy\right]^{0.5}$$

where w(x,y) is the wavefront aberration function defined over pupil coordinates x,y, A=pupil area, and the integration is performed over the domain of the entire pupil. Computationally, $RMS_w$ is the standard deviation of the values of wavefront error specified at various pupil locations.

PV=Peak-to-Valley Difference (Microns)

$$PV=\max(w(x,y))-\min(w(x,y))$$

PV is the difference between the highest and lowest points in the aberration map.

Slope Metrics

Wavefront slope is a vector-valued function of pupil position that requires two maps for display. Wavefront slopes may be interpreted as transverse ray aberrations that blur the image.

The root-mean-squared value of a slope map is a measure of the spreading of light rays that blur the image in one direction. The total RMS value computed for both slope maps taken together is thus a convenient metric of wavefront quality that may be interpreted in terms of the size of the spot diagram.

$RMS_s$=Root-Mean-Squared Wavefront Slope Computed Over the Whole Pupil (arcmin)

$$RMS_s = \left[\frac{1}{A}\int_{pupil}(w_x(x,y) - \overline{w}_x)^2 + (w_y(x,y) - \overline{w}_y)^2 dxdy\right]^{0.5}$$

where $w_x$=dw/dx; $w_y$=dw/dy are the partial spatial derivatives (i.e. slopes) of w(x,y) and A=pupil area.

Curvature Metrics

Wavefront curvature describes focusing errors that blur the image. To form a good image at some finite distance, wavefront curvature must be the same everywhere across the pupil. A perfectly flat wavefront will have zero curvature everywhere, which corresponds to the formation of a perfect image at infinity. Like wavefront slope, wavefront curvature is a vector-valued function of position that requires more than one map for display. The principal curvatures at every point can be derived from maps of mean curvature M(x,y) and Gaussian curvature G(x,y) as follows.

$$M(x,y) = \frac{k_1(x,y) + k_2(x,y)}{2}$$

$$G(x,y) = k_1(x,y) \cdot k_2(x,y)$$

where the principal curvature maps $k1(x,y)$, $k2(x,y)$ are computed from M and G using $$k_1,k_2 = M(x,y) \pm \sqrt{M^2(x,y) - G(x,y)}$$

The Gaussian and mean curvature maps may be obtained from the spatial derivatives of the wavefront aberration map using textbook formulas.

Given the principal curvature maps, the dimensionality of wavefront curvature's reduced by computing blur strength at every pupil location. A power vector P=(M, $J_0$, $J_{45}$) is a 3-dimensional vector whose coordinates correspond to the spherical equivalent (M), the normal component of astigmatism ($J_0$) and the oblique component of astigmatism ($J_{45}$). Experiments have shown that the length of the power vector, which is the definition of blur strength, is a good scalar measure of the visual impact of sphero-cylindrical blur. Thus, a map of the length of the power-vector representation of a wavefront at each point in the pupil may be called a blur-strength map.

To compute the blur-strength map first use the principal curvature maps to compute the astigmatism map.

$$J(x,y) = \frac{k_1(x,y) - k_2(x,y)}{2}$$

and then combine the astigmatism map with the mean curvature map using the Pythagorean formula to produce a blur strength map.

$$B(x,y) = \sqrt{M^2(x,y) + J^2(x,y)}$$

The spatial average of this blur strength map is a scalar value that represents the average amount of focusing error in the system that is responsible for image degradation, $B_{ave}$=Average Blur Strength (Diopters)

$$B_{ave} = \frac{1}{\text{pupil area}}\int_{pupil} B(x,y)dxdy$$

Pupil Fraction Metrics

Metrics of wavefront quality can be defined based on the concept of pupil fraction. Pupil fraction is defined as the fraction of the pupil area for which the optical quality of the eye is reasonably good. A large pupil fraction is desirable because it means that most of the light entering the eye will contribute to a good-quality retinal image.

$$\text{Pupil Fraction} = \frac{\text{Area of good pupil}}{\text{Total area of pupil}}$$

There are two general methods for determining the area of the good pupil. The first method, called the "critical pupil" or "central pupil" method examines the wavefront inside a sub-aperture that is concentric with the eye's pupil. Imagine starting with a small sub-aperture where image quality is guaranteed to be good (i.e. diffraction-limited) and then expanding the aperture until some criterion of wavefront quality is reached. This endpoint is the critical diameter, which can be used to compute the pupil fraction (critical pupil method) as follows $$PF_c = \left[\frac{\text{critical diameter}}{\text{pupil diameter}}\right]^2$$

The above equation requires some criterion for what is meant by "good wavefront quality". For example, the criterion could be based on the wavefront aberration map, $PFW_c=PF_c$ when Critical Pupil is Defined as the Concentric Area for which $RMS_w<$Criterion (e.g. $\lambda/4$)

Alternatively, the criterion for good wavefront quality could be based on wavefront slope, $PFS_c=PF_c$ when Critical Pupil is Defined as the Concentric Area for which $RMS_s<$Criterion (e.g. 1 arcmin)

Or the criterion could be based on wavefront curvature as represented by the blur strength map, $PFC_c=PF_c$ when Critical Pupil is Defined as the Concentric Area for which $B_{ave}<$Criterion (e.g. 0)

The second general method for determining the area of the good pupil is called the "tessellation" or "whole pupil" method. We imagine tessellating the entire pupil with small sub-apertures and then labeling each sub-aperture as good or bad according to some criterion. The total area of all those sub-apertures labeled "good" defines the area of the good pupil from which we compute pupil fraction as $$PF_t = \frac{\text{Area of good subapertures}}{\text{Total area of pupil}}$$

As with the concentric metrics, implementation of this equation requires criteria for deciding if the wavefront over a sub-aperture is "good". For example, the criterion could be based on the wavefront aberration function, $PFW_t=PF_t$ when a "Good" Sub-Aperture Satisfies the Criterion Pv<Criterion (e.g. $\lambda/4$)

Alternatively, the criterion could be based on wavefront slope, $PFS_t=PF_t$ when a "Good" Sub-Aperture Satisfies the Criterion Horizontal Slope and Vertical Slope are Both<Criterion (e.g. 1 arcmin)

Or the criterion could be based on wavefront curvature as summarized by blur strength, $PFCt=PF_t$ when a "Good" Sub-Aperture Satisfies the Criterion B<Criterion (e.g. 0.25D) Metrics of Image Quality for Point Objects A perfect optical system images a point object into a compact, high-contrast retinal image. The image of a point object is called a point-spread function (PSF). The PSF is calculated as the squared magnitude of the inverse Fourier transform of the pupil function P(x,y), defined as $$P(x,y)=A(x,y)\exp(ikW(x,y))$$

where k is the wave number ($2\pi$/wavelength) and A(x,y) is an optional apodization function of pupil coordinates x,y. When computing the physical retinal image at the entrance apertures of the cone photoreceptors, the apodization function is usually omitted. However, when computing the visual effectiveness of the retinal image, the waveguide nature of cones must be taken into account. These waveguide properties cause the cones to be more sensitive to light entering the middle of the pupil than to light entering at the margin of the pupil. It is common practice to model this phenomenon as an apodizing filter with transmission A(x,y) in the pupil plane.

Scalar metrics of image quality that capture the quality of the PSF in aberrated eyes are designed to capture the dual attributes of compactness and contrast. The first 5 metrics listed below measure spatial compactness and in every case small values of the metric indicate a compact PSF of good quality. The last 6 metrics measure contrast and in every case large values of the metric indicate a high-contrast PSF of good quality. Most of the metrics are completely optical in character, but a few also include knowledge of the neural component of the visual system. Several of these metrics are 2-dimensional extensions of textbook metrics defined for 1-dimensional impulse response functions. Many of the metrics are normalized by diffraction-limited values and therefore are unitless.

D50=Diameter of a Circular Area Centered on PSF Peak which Captures 50% of the Light Energy (arcmin)

The value of D50 is equal to the radius r, where r is defined implicitly by:

$$\int_0^{2\pi}\int_0^r PSF_N(r,\theta)rdrd\theta = 0.5$$

where $PSF_N$ is the normalized (i.e. total intensity=1) point-spread function centered on the origin (i.e. peak of $PSF_N$ is located at r=0). This metric ignores the light outside the central 50% region, and thus is insensitive to the shape of the PSF tails.

EW=Equivalent Width of Centered PSF (arcmin)

The equivalent width of the PSF is the diameter of the circular base of that right cylinder which has the same volume as the PSF and the same height. The value of EW is given by:

$$EW = \left[\frac{4\int_{pupil} PSF(x,y)dxdy}{\pi PSF(x_0,y_0)}\right]^{0.5}$$

where $x_0$, $y_0$ are the coordinates of the peak of the PSF. In this and following equations, x,y are spatial coordinates of the retinal image, typically specified as visual angles subtended at the eye's nodal point. Note that although EW describes spatial compactness, it is computed from PSF contrast. As the height falls the width must increase to maintain a constant volume under the PSF.

SM=Square Root of Second Moment of Light Distribution (arcmin)

This metric is analogous to the moment of inertia of a distribution of mass. It is computed as $$SM = \left[\frac{\int_{pupil}(x^2+y^2)PSF(x,y)dxdy}{\int_{pupil}PSF(x,y)dxdy}\right]^{0.5}$$

Unlike D50 above, this compactness metric is sensitive to the shape of the PSF tails.

HWHH=Half Width at Half Height (arcmin)

This metric is the average width of every cross-section of the PSF. It is computed as $$HWHH = \left[\frac{1}{\pi}\int_{pupil}C(x,y)dxdy\right]^{0.5}$$

where C(x,y)=1 if PSF(x,y)>max(PSF)/2, otherwise C(x,y)=0.

CW=Correlation Width of Light Distribution (arcmin)

This metric is the HWHH of the autocorrelation of the PSF. It is computed as $$CW = \left[\frac{1}{\pi}\int_{-\infty}^{\infty}\int_{-\infty}^{\infty}Q(x,y)dxdy\right]^{0.5}$$

where Q(x,y)=1 if PSF●PSF> max(PSF●PSF)/2, otherwise Q(x,y)=0. In this expression, PSF●PSF is the autocorrelation of the PSF.

SRX=Strehl Ratio Computed in Spatial Domain

This widely-used metric is typically defined with respect to the peak of the PSF, rather than the coordinate origin. It is computed as $$SRX = \frac{\max(PSF)}{\max(PSF_{DL})}$$

where $PSF_{DL}$ is the diffraction-limited PSF for the same pupil diameter.

LIB=Light-in-the-Bucket

The value of this metric is the percentage of total energy falling in an area defined by the core of a diffraction-limited PSF, $$LIB = \int_{DLcore}PSF_N(x,y)dxdy$$

where $PSF_N$ is the normalized (i.e. total intensity=1) point-spread function. The domain of integration is the central core of a diffraction-limited PSF for the same pupil diameter.

STD=Standard Deviation of Intensity Values in the PSF, Normalized to Diffraction-Limited value This metric measures the variability of intensities at various points in the PSF, $$STD = \frac{\left[\int_{psf}(PSF(x,y)-\overline{PSF})^2dxdy\right]^{0.5}}{\left[\int_{psf}(PSF_{DL}(x,y)-\overline{PSF_{DL}})^2dxdy\right]^{0.5}}$$

where $PSF_{DL}$ is the diffraction-limited point-spread function. The domain of integration is a circular area centered on the PSF peak and large enough in diameter to capture most of the light in the PSF.

ENT=Entropy of the PSF

This metric is inspired by an information-theory approach to optics.

$$ENT = -\int_{psf}PSF(x,y)\ln(PSF(x,y))dxdy$$

NS=Neural Sharpness

This metric was introduced by Williams as a way to capture the effectiveness of a PSF for stimulating the neural portion of the visual system. This is achieved by weighting the PSF with a spatial sensitivity function that represents the neural visual system and then integrating the result over the domain of the PSF. Here we normalize the result by the corresponding value for a diffraction-limited PSF to achieve a metric that is analogous to the Strehl ratio computed for a neurally-weighted PSF, $$NS = \frac{\int_{psf}PSF(x,y)g(x,y)dxdy}{\int_{psf}PSF_{DL}(x,y)g(x,y)dxdy}$$

where g(x,y) is a bivariate-Gaussian, neural weighting-function. A profile of this weighting function shows that it effectively ignores light outside of the central 4 arc minutes of the PSF.

VSX=Visual Strehl Ratio Computed in the Spatial Domain.

Like the neural sharpness metric, the visual Strehl ratio weights the PSF with a neural weighting function before computing the Strehl ratio. The difference between NS and VSX is in the choice of weighting functions.

$$VSX = \frac{\int_{psf}PSF(x,y)N(x,y)dxdy}{\int_{psf}PSF_{DL}(x,y)N(x,y)dxdy}$$

where N(x,y) is a bivariate neural weighting function equal to the inverse Fourier transform of the neural contrast sensitivity function for interference fringes. With this metric, light outside of the central 3 arc minutes of the PSF doubly detracts from image quality because it falls outside the central core and within an inhibitory surround. This is especially so for light just outside of the central 3 arc minutes in that slightly aberrated rays falling 2 arc minutes away from the PSF center are more detrimental to image quality than highly aberrated rays falling farther from the center.

Metrics of Image Quality for Grating Objects

Unlike point objects, which can produce an infinite variety of PSF images depending on the nature of the eye's aberrations, small patches of grating objects always produce sinusoidal images no matter how aberrated the eye. Consequently, there are only two ways that aberrations can affect the image of a grating patch: they can reduce the contrast or translate the image sideways to produce a phase-shift. In general, the amount of contrast attenuation and the amount of phase shift both depend on the grating's spatial frequency. This variation of image contrast with spatial frequency for an object with 100% contrast is called a modulation transfer function (MTF). The variation of image phase shift with spatial frequency is called a phase transfer function (PTF). Together, the MTF and PTF comprise the eye's optical transfer function (OTF). The OTF is computed as the Fourier transform of the PSF.

Optical theory explains that any object can be conceived as the sum of gratings of various spatial frequencies, contrasts, phases and orientations. In this context the optical system of the eye is considered a filter that lowers the contrast and changes the relative position of each grating in the object spectrum as it forms a degraded retinal image. A high-quality OTF is therefore indicated by high MTF values and low PTF values. Scalar metrics of image quality in the frequency domain are based on these two attributes of the OTF.

SFcMTF=Spatial Frequency Cutoff of Radially-Averaged Modulation-Transfer Function (rMTF)

Cutoff SF is defined here as the intersection of the radially averaged MTF (rMTF) and the neural contrast threshold function. The rMTF is computed by integrating the full 2-dimensional MTF over orientation. This metric does not capture spatial phase errors in the image because rMTF is not affected by the PTF portion of the OTF.

SFcMTF=highest spatial freq. for which rMTF>neural threshold where $$rMTF(f) = \frac{1}{2\pi}\int_0^{2\pi} \text{abs}(OTF(f,\phi))d\phi$$

and OTF(f,φ) is the optical transfer function for spatial frequency coordinates f (frequency) and φ (orientation).

SFcOTF=Cutoff Spatial Frequency of Radially-Averaged Optical-Transfer Function (rOTF).

The radially-averaged OTF is determined by integrating the full 2-dimensional OTF over orientation. Since the PTF component of the OTF is taken into account when computing rOTF, this metric is intended to capture spatial phase errors in the image.

SFcOTF=lowest spatial freq. for which rOTF<neural threshold where $$rOTF(f) = \frac{1}{2\pi}\int_0^{2\pi} OTF(f,\phi)d\phi$$

and OTF(f,φ) is the optical transfer function for spatial frequency coordinates f (frequency) and φ (orientation). Since the OTF is a complex-valued function, integration is performed separately for the real and imaginary components. Conjugate symmetry of the OTF ensures that the imaginary component vanishes, leaving a real-valued result.

The primary distinction between metrics SFcMTF and SFcOTF is that SFcMTF ignores phase errors, with phase-altered and even phase-reversed modulations treated the same as correct-phase modulations. For example, with an amplitude-oscillating and phase-reversing defocused OTF, the SFcMTF identifies the highest frequency for which modulation exceeds threshold, irrespective of lower frequency modulation minima and phase reversals. By contrast, SFcOTF identifies the highest SF within the correct-phase, low-frequency portion of the OTF. This allows "spurious resolution" to be discounted when predicting visual performance on tasks of spatial resolution and pattern discrimination.

AreaMTF=Area of Visibility for rMTF (Normalized to Diffraction-Limited Case).

The area of visibility in this context is the region lying below the radially averaged MTF and above the neural contrast threshold function. The normalized metric is computed as $$AreaMTF = \frac{\int_0^{cutoff} rMTF(f)df - \int_0^{cutoff} T_N(f)df}{\int_0^{cutoff} rMTF_{DL}(f)df - \int_0^{cutoff} T_N(f)df}$$

where $T_N$ is the neural contrast threshold function, which equals the inverse of the neural contrast sensitivity function. When computing area under rMTF, phase-reversed segments of the curve count as positive area. This is consistent with our definition of SFcMTF as the highest frequency for which rMTF exceeds neural threshold. This allows "spurious resolution" to be counted as beneficial when predicting visual performance for the task of contrast detection.

AreaOTF=Area of Visibility for rOTF (Normalized to Diffraction-Limited Case).

The area of visibility in this context is the region that lies below the radially averaged OTF and above the neural contrast threshold function. The normalized metric is computed as $$AreaOTF = \frac{\int_0^{cutoff} rOTF(f)df - \int_0^{cutoff} T_N(f)df}{\int_0^{cutoff} rOTF_{DL}(f)df - \int_0^{cutoff} T_N(f)df}$$

where $T_N$ is the neural contrast threshold function defined above. Since the domain of integration extends only to the cutoff spatial frequency, phase-reversed segments of the curve do not contribute to area under rOTF. This is consistent with the definition of SFcOTF as the lowest frequency for which rOTF is below neural threshold. This metric would be appropriate for tasks in which phase reversed modulations (spurious resolution) actively interfere with performance.

SRMTF=Strehl Ratio Computed in Frequency Domain (MTF Method)

The Strehl ratio is often computed in the frequency domain on the strength of the central ordinate theorem of Fourier analysis. This theorem states that the central value of a function is equal to the area (or volume, in the 2-dimensional case) under its Fourier transform. Since the OTF is the Fourier transform of the PSF, we may conclude that the volume under the OTF is equal to the value of the PSF at the coordinate origin. In many cases the PTF portion of the OTF is unknown, which has led to the popular substitution of the MTF for the OTF in this calculation. Although popular, this method lacks rigorous justification because MTF=|OTF|. This non-linear transformation destroys the Fourier-transform relationship between the spatial and frequency domains that is the basis of the central ordinate theorem, which in turn is the justification for computing SR in the frequency domain.

$$SRMTF = \frac{\int_{-\infty}^{\infty}\int_{-\infty}^{\infty} MTF(f_x, f_y) df_x df_y}{\int_{-\infty}^{\infty}\int_{-\infty}^{\infty} MTF_{DL}(f_x, f_y) df_x df_y}$$

Strehl ratio computed by the MTF method is equivalent to the Strehl ratio for a hypothetical PSF that is well-centered with even symmetry computed as the inverse Fourier transform of MTF (which implicitly assumes. PTF=0). Thus, in general, SRMTF is only an approximation of the actual Strehl ratio computed in the spatial domain (SRX).

SROTF=Strehl Ratio Computed in Frequency Domain (OTF Method)

The Strehl ratio computed by the OTF method will accurately compute the ratio of heights of the PSF and a diffraction-limited PSF at the coordinate origin. However, the peak of the PSF does not necessarily occur at the coordinate origin established by the pupil function. Consequently, the value of SROTF is not expected to equal SRX exactly, except in those special cases where the peak of the PSF occurs at the coordinate origin.

$$SROTF = \frac{\int_{-\infty}^{\infty}\int_{-\infty}^{\infty} OTF(f_x, f_y) df_x df_y}{\int_{-\infty}^{\infty}\int_{-\infty}^{\infty} OTF_{DL}(f_x, f_y) df_x df_y}$$

VSMTF=Visual Strehl Ratio Computed in Frequency Domain (MTF Method)

This metric is similar to the MTF method of computing the Strehl ratio, except that the MTF is weighted by the neural contrast sensitivity function $CSF_N$, $$VSMTF = \frac{\int_{-\infty}^{\infty}\int_{-\infty}^{\infty} CSF_N(f_x, f_y) \cdot MTF(f_x, f_y) df_x df_y}{\int_{-\infty}^{\infty}\int_{-\infty}^{\infty} CSF_N(f_x, f_y) \cdot MTF_{DL}(f_x, f_y) df_x df_y}$$

In so doing, modulation in spatial frequencies above the visual cut-off of about 60 c/deg is ignored, and modulation near the peak of the CSF (e.g. 6 c/deg) is weighted maximally. It is important to note that this metric gives very little weight to visible, high spatial-frequencies employed in typical visual acuity testing (e.g. 40 c/deg in 20/15 letters). Visual Strehl ratio computed by the MTF method is equivalent to the visual Strehl ratio for a hypothetical PSF that is well-centered with even symmetry computed as the inverse Fourier transform of MTF (which implicitly assumes PTF=0). Thus, in general, VSMTF is only an approximation of the visual Strehl ratio computed in the spatial domain (VSX).

VSOTF=Visual Strehl Ratio Computed in Frequency Domain (OTF Method)

This metric is similar to the OTF method of computing the Strehl ratio, except that the OTF is weighted by the neural contrast sensitivity function $CSF_N$, $$VSOTF = \frac{\int_{-\infty}^{\infty}\int_{-\infty}^{\infty} CSF_N(f_x, f_y) \cdot OTF(f_x, f_y) df_x df_y}{\int_{-\infty}^{\infty}\int_{-\infty}^{\infty} CSF_N(f_x, f_y) \cdot OTF_{DL}(f_x, f_y) df_x df_y}$$

This metric differs from VSX by emphasizing image quality at the coordinate origin, rather than at the peak of the PSF.

VOTF=Volume Under OTF Normalized by the Volume Under MTF

This metric is intended to quantify phase shifts in the image. It does so by comparing the volume under the OTF to the volume under the MTF.

$$VOTF = \frac{\int_{-\infty}^{\infty}\int_{-\infty}^{\infty} OTF(f_x, f_y) df_x df_y}{\int_{-\infty}^{\infty}\int_{-\infty}^{\infty} MTF(f_x, f_y) df_x df_y}$$

Since the MTF≦the real part of the OTF, this ratio is always ≦1. Creation of this metric was inspired by a measure of orientation bias of the receptive fields of retinal ganglion cells.

VNOTF=Volume Under Neurally-Weighted OTF, Normalized by the Volume Under Neurally-Weighted MTF This metric is intended to quantify the visually-significant phase shifts in the image. It does so by weighting the MTF and OTF by the neural contrast sensitivity function before comparing the volume under the OTF to the volume under the MTF.

$$VNOTF = \frac{\int_{-\infty}^{\infty}\int_{-\infty}^{\infty} CSF(f_x, f_y) \cdot OTF(f_x, f_y) df_x df_y}{\int_{-\infty}^{\infty}\int_{-\infty}^{\infty} CSF(f_x, f_y) \cdot MTF(f_x, f_y) df_x df_y}$$

Polychromatic Metrics

The wavefront aberration function is a monochromatic concept. If a source emits polychromatic light, then wavefront aberration maps for each wavelength are treated separately because lights of different wavelengths are mutually incoherent and do not interfere. For this reason, metrics of wavefront quality do not generalize easily to the case of polychromatic light. This lack of generality is a major limitation of the wavefront metric approach to quantifying the optical quality of an eye.

To the contrary, polychromatic metrics of image quality for point objects are easily derived from their monochromatic counterparts. The polychromatic point-spread function $PSF_{poly}$ is a weighted sum of the monochromatic spread functions $PSF(x,y,\lambda)$, $$PSF_{poly} = \int V(\lambda) PSF(x,y,\lambda) d\lambda$$

where the weighting function $V(\lambda)$ is the luminous efficiency function that describes how visual sensitivity to monochromatic light varies with wavelength $\lambda$. Given this definition, $PSF_{poly}$ may be substituted for PSF in any of the equations given above to produce new, polychromatic metrics of image quality. In addition to these luminance metrics of image quality, other metrics can be devised to capture the changes in color appearance of the image caused by ocular aberrations. For example, the chromaticity coordinates of a point source may be compared to the chromaticity coordinates of each point in the retinal PSF and metrics devised to summarize the differences between image chromaticity and object chromaticity. Such metrics may prove useful in the study of color vision.

Given the polychromatic point-spread function defined above in eqn. (35), a polychromatic optical transfer function $OTF_{poly}$ may be computed as the Fourier transform of $PSF_{poly}$. Substituting this new function for OTF (and its magnitude for MTF) in any of the equations given above will produce new metrics of polychromatic image quality defined in the frequency domain.

D. Adjusting the Calculated Prescription

As previously noted, an optimized prescription that is clinically preferable must include such considerations as depth of focus at distance and the refractionist's rule "maximum plus to best visual acuity," should consider the prior prescription used by the patient, should consider how the patient plans to use the prescription, and may take into account other clinical considerations such as different prescriptions for the two eyes of the same patient.

In practice, these considerations can be introduced into the calculations when the original calculation is made. For example, in instances where the clinician knows that the prescription will be used for sunglasses or for night driving, the pupil size may be adjusted prior to performing the calculation. However, other clinical considerations are more appropriately suited to adjusting the ideal prescription for infinitely distant objects after the calculation has been made. For example, adjusting an ideal prescription to maximize the usable depth of focus is typically performed by adjusting the spherical lens power of a prescription so that the power is slightly less negative (in the case of myopia) or slightly more positive (in the case of hyperopia) than the lens required to make the prescription the optical ideal. Therefore, a myopic patient (nearsighted) will typically have her prescription adjusted to be 0.2-0.5 diopters less negative than the ideal prescription, and a hyperopic patient (farsighted) will typically have her prescription adjusted to be 0.2 to 0.5 diopters more positive than her ideal prescription. The notion that retinal image optimization for infinite distance is "ideal" is incorrect.

First, for younger eyes in which accommodation fluctuates, setting the mean to optimize infinity is less than ideal because it does not take into account the fact that all real objects are located at a finite distance.

Performance of the Method

It will be further appreciated that performance of the above methods can be performed in an automated fashion through the use of a computer processor to collect the aberrometric data and perform the noted calculations.

Further, it should be noted that in another embodiment of the present invention, the method of performing method may include the additional step of eliminating the bulk of the spherical and cylindrical refractive errors by nulling the second-order Zernike coefficients or nulling the second-order Seidel coefficients in the aberrometric map. From this higher-order aberration map, optimization of the selected metrics can be performed. If the metric to be optimized is the root-mean-square metric, the prescription can be computed directly from the value of the second-order Zernike coefficient. If the clinician chooses to optimize the metric using the equivalent quadratic fitting method described above, the prescription can be computed directly from the values of the second-order and fourth-order Zernike coefficients. However, if the clinician could optionally perform three separate through-focus calculations on the higher-order aberration map to obtain the values of second-order coefficients that separately maximize the chosen metric of optical quality. In principle, these through-focus calculations are performed by selecting a value of one of the second-order coefficients from a pre-selected set of values that correspond to clinically meaningful (e.g. ⅛ Diopter) steps of focus (Z2\0), orthoastigmatsm (Z2\+2), or oblique astigmatism (Z2\−2). The prescription then, is the sum of optimum values obtained and the original second order aberration coefficients nulled to create the higher order aberration map. However, the computer calculations are not constrained to any specific increments of power (e.g. ⅛ diopter) and may, in fact, use much finer steps to improve resolution. Alternatively, the results for discrete steps may be interpolated by suitable computer algorithms to achieve very high resolution.

Although the present invention has been described in considerable detail with reference to certain preferred versions thereof, other versions are possible. Therefore, the spirit and scope of the appended claims should not be limited to the description of the preferred versions contained herein. Further, it will be appreciated that the embodiments of the present invention provide a method for objectively calculating an optimal subjective clinical prescription with little iterative trial and error, as well as utilizing a method that allows a clinician to optimize an optical prescription using several metrics of optical quality. Further, it will be appreciated that the embodiments of the present invention provide a means for adjusting an objective calculation to take into account maximized depth of focus, as well as other clinical information such as patient data and environmental data. For example, the patient can also quantify the optical corrections that will achieve any desired depth of focus by manipulating the eye+lens higher order aberrations using the same virtual through focus methods. This would be particularly useful for the correction of presbyopia (fixed focus eye). Finally, it will be appreciated that the embodiments of the present invention provide a method for optimizing a clinical prescription that requires less computing power than previous methods and provide improved flexibility over prior art methods. This approach not only provides reduced computational requirements, but also vastly improved flexibility in that it can be used to do more than just optimize sphero-cylindrical prescriptions, but also the depth of focus, and as such enable automated refractions for a range of levels of emerging presbyopia and visual environments.

What is claimed is:

1. A method for optimizing a refractive prescription without using subjective refractions, the method comprising the steps of:
   a. obtaining aberrometric data from a patient by way of an aberrometer; and
   b. selecting an objective image quality metric, wherein the objective metric of image quality is selected from a group consisting of average blur strength ("$B_{ave}$"), pupil fraction when the critical pupil is defined as the concentric area for which $RMS_w$ is less than a criterion ("$PFW_c$"), pupil fraction when the critical pupil is defined as the concentric area for which $RMS_s$ is less than the criterion ("$PFS_c$"), pupil fraction when the critical pupil is defined as the concentric area for which $B_{ave}$ is less than the criterion ("$PFC_c$"), area of a good subaperature divided by the total area of a pupil when the good subaperature satisfies a criterion PV<the criterion ("$PFW_t$"), area of the good subaperature divided by the total area of a pupil when the good subaperature satisfies a criterion horizontal slope and vertical slope are both less than the criterion ("$PFS_t$"), area of the good subaperature divided by a total area of a pupil when the good subaperture satisfies the criterion B less than the criterion ("$PFC_t$"), visual strehl ratio computed in a spatial domain ("VSX"), visual strehl ratio computed in a frequency domain by modulation transfer function method ("VSMTF"), visual strehl ratio computed in the frequency domain by optical-transfer function method ("VSOTF"), volume under optical transfer function normalized by a volume under modulation-transfer function ("VOTF"), volume under neurally-weighted optical transfer function normalized by the volume under neurally-weighted modulation-transfer function ("VNOTF");

c. computing the objective image quality metric from the aberrometric data;

d. iteratively modifying the level of spherical and cylindrical defocus of the abberometric data;

e. computing the modified objective image quality metric from the modified abberometric data;

f. repeating steps c and d until the modified objective image quality metric is optimized; and g. generating at least one clinical refractive sphereocylindrical prescription for the patient based on the optimized objective image quality metric.

2. The method of claim 1, further comprising the step of adjusting the refractive prescription to maximize the utilization of the patient's depth of field if the aberrometric data suggests that the patient's vision is myopic.

3. The method of claim 1, further comprising the step of adjusting the ideal optic prescription to maximize the utilization of the patient's depth of field if the aberrometric data suggests that the patient's vision is hyperopic.

4. The method of claim 1, further comprising the step of evaluating the results and allowing a user to determine whether the prescription should be further optimized.

5. The method of claim 1, further comprising the step of selecting one of a plurality of optic prescriptions.

6. The method of claim 1, further comprising the steps of:
a. obtaining patient data; and
b. utilizing the patient data to optimize a clinical refractive prescription.

7. The method of claim 1, further comprising the steps of:
a. obtaining environmental data; and
b. utilizing the environmental data to optimize a clinical refractive prescription.

8. The method of claim 1, wherein the equivalent quadratic fitting calculation nulls the second-order Zernike coefficients in the aberometric map.

9. The method of claim 1, wherein the equivalent quadratic fitting calculation nulls the second-order Seidel coefficients in the aberometric map.

10. A method for optimizing a refractive prescription without using subjective refractions, the method comprising the steps of:
a. obtaining aberrometric data from a patient by way of an aberrometer;
b. selecting a metric of optimized image quality, wherein the metric of image quality if selected from a group consisting of average blur strength ("$B_{ave}$"), pupil fraction when the critical pupil is defined as the concentric area for which $RMS_w$ is less than a criterion ("$PFW_c$"), pupil fraction when the critical pupil is defined as the concentric area for which $RMS_s$ is less than the criterion ("$PFS_c$"), pupil fraction when the critical pupil is defined as the concentric area for which $B_{ave}$ is less than the criterion ("$PFC_c$"), area of a good subaperature divided by the total area of a pupil when the good subaperature satisfies a criterion PV<the criterion ("$PFW_t$"), area of the good subaperture divided by the total area of a pupil when the good subaperature satisfies a criterion horizontal slope and vertical slope are both less than the criterion ("$PFS_t$"), area of the good subaperature divided by a total area of a pupil when the good subaperature satisfies the criterion B less than the criterion ("$PFC_t$"), visual strehl ratio computed in a spatial domain ("VSX"), visual strehl ratio computed in a frequency domain by modulation transfer function method ("VSMTF"), visual strehl ratio computed in the frequency domain by optical-transfer function method ("VSOTF"), volume under optical transfer function normalized by a volume under modulation-transfer function ("VOTF"), volume under neurally-weighted optical transfer function normalized by the volume under neurally-weighted modulation-transfer function ("VNOTF");

c. generating an aberration map from the aberrometric data;

d. simulating a through focus experiment; and e. computing an ideal optic prescription using the metric of optimized image quality; whereby the method for optimizing a refractive prescription occurs without the use of subjective refractions.

11. The method of claim 10, further comprising the step of adjusting the ideal optic prescription to maximize the utilization of the eye's depth of field if the aberrometric data suggests that the patient's vision is myopic.

12. The method of claim 10, further comprising the step of adjusting the ideal optic prescription to maximize the utilization of the eye's depth of field if the aberrometric data suggests that the patient's vision is hyperopic.

13. The method of claim 10, wherein the step of simulating a through focus experiment is performed by a computer processor.

14. The method of claim 10, further comprising the step of evaluating the results and allowing a user to determine whether the prescription should be further optimized.

15. The method of claim 10, further comprising the steps of:
a. obtaining patient data; and
b. utilizing the patient data to optimize a clinical refractive prescription.

16. The method of claim 10, further comprising the steps of:
a. obtaining environmental data; and
b. utilizing the environmental data to optimize a clinical refractive prescription.

17. The method of claim 10, comprising the additional step of recalculating metrics for each condition in the through focus simulation.

18. The method of claim 17, further comprising the step of selecting a prescription that maximizes the chosen metric.

19. The method of claim 18, wherein the prescription that maximizes the chosen metric is maximized for a specific distance.

20. The method of claim 18, wherein the prescription that maximizes the chosen metric is maximized to achieve a desired trade-off between maximal quality and depth of focus.

21. The method of claim 10, further comprising the step of eliminating at least one spherical and cylindrical refractive error by nulling the second-order Zernike coefficients in the aberrometric map.

22. The method of claim 10, further comprising the step of eliminating at least one spherical and cylindrical refractive error by nulling the second-order Seidel coefficients in the aberrometric map.

23. A method for optimizing a refractive prescription without using subjective refractions, the method comprising the steps of:
   a. obtaining aberrometric data from a patient by way of an aberrometer;
   b. selecting a metric of optimized image quality, wherein the metric is selected from a group consisting of average blur strength ("$B_{ave}$"), pupil fraction when the critical pupil is defined as the concentric area for which $RMS_w$ is less than a criterion ("$PFW_c$"), pupil fraction when the critical pupil is defined as the concentric area for which $RMS_s$ is less than the criterion ("$PFS_c$"), pupil fraction when the critical pupil is defined as the concentric area for which $B_{ave}$ is less than the criterion ("$PFC_c$"), area of a good subaperature divided by the total area of a pupil when the good subaperature satisfies a criterion PV<the criterion ("$PFW_t$"), area of the good subaperature divided by the total area of a pupil when the good subaperature satisfies a criterion horizontal slope and vertical slope are both less than the criterion ("$PFS_t$"), area of the good subaperature divided by a total area of a pupil when the good subaperature satisfies the criterion B less than the criterion ("$PFC_t$"), visual strehl ratio computed in a spatial domain ("VSX"), visual strehl ratio computed in a frequency domain by modulation transfer function method ("VSMTF"), visual strehl ratio computed in the frequency domain by optical-transfer function method ("VSOTF"), volume under optical transfer function normalized by a volume under modulation-transfer function ("VOTF"), volume under neurally-weighted optical transfer function normalized by the volume under neurally-weighted modulation-transfer function ("VNOTF");
   c. generating an aberration map from the aberrometric data;
   d. simulating a through focus experiment; whereby the method for optimizing a refractive prescription occurs without the use of subjective refractions;
   e. calculating metrics for each condition in the through focus simulation; and
   f. selecting a prescription that maximizes the chosen metric.

24. The method of claim 23, further comprising the steps of:
   adjusting at least one variable of the abberometric data; and
   recalculating the metrics for each condition in the through focus simulation.

* * * * *

UNITED STATES PATENT AND TRADEMARK OFFICE
CERTIFICATE OF CORRECTION

PATENT NO. : 7,857,451 B2  Page 1 of 1
APPLICATION NO. : 10/582470
DATED : December 28, 2010
INVENTOR(S) : Larry N. Thibos et al.

It is certified that error appears in the above-identified patent and that said Letters Patent is hereby corrected as shown below:

Column 1, lines 7-11 of the Patent should be replaced with the following Statement Regarding Federally Sponsored Research and Development.

"This invention was made with government support under EY005109 and EY008520 awarded by the National Institutes of Health. The U.S. Government has certain rights in the invention."

Signed and Sealed this
First Day of March, 2011

David J. Kappos
*Director of the United States Patent and Trademark Office*